United States Patent [19]
Pippert

[11] Patent Number: 5,263,367
[45] Date of Patent: Nov. 23, 1993

[54] METHOD AND APPARATUS FOR DETERMINING DELIVERY AMOUNTS AND RATES OF PUMPS IN THE MEDICOTECHNICAL FIELD

[75] Inventor: Manfred Pippert, Glashütten, Fed. Rep. of Germany

[73] Assignee: Medical Support GmbH, Rodgau, Fed. Rep. of Germany

[21] Appl. No.: 818,065

[22] Filed: Jan. 8, 1992

[30] Foreign Application Priority Data

Jan. 8, 1991 [DE] Fed. Rep. of Germany ....... 4100317

[51] Int. Cl.$^5$ ........................................... G01M 19/00
[52] U.S. Cl. ........................................... 73/168; 73/3
[58] Field of Search ........................... 73/168, 3

[56] References Cited

U.S. PATENT DOCUMENTS

| | | |
|---|---|---|
| 2,566,742 | 9/1951 | Odell .................................. 73/168 |
| 2,795,950 | 6/1957 | Liddell ............................... 73/168 |
| 3,350,934 | 11/1967 | Orkney, Jr. et al. ................. 73/168 |
| 4,461,169 | 7/1984 | Augustin ............................ 73/119 A |
| 4,705,459 | 11/1987 | Buisine et al. ...................... 73/168 |
| 4,856,343 | 8/1989 | Hon ................................... 73/168 |
| 5,140,862 | 8/1992 | Pappalardo ......................... 73/3 |

FOREIGN PATENT DOCUMENTS

| | | | |
|---|---|---|---|
| 0853162 | 8/1981 | U.S.S.R. ............................. | 73/168 |
| 1513196 | 10/1989 | U.S.S.R. ............................. | 73/168 |
| 2206416 | 1/1989 | United Kingdom ..................... | 73/3 |
| 2224479 | 5/1990 | United Kingdom ..................... | 73/3 |

Primary Examiner—William A. Cuchlinski, Jr.
Assistant Examiner—Diego F. F. Gutierrez
Attorney, Agent, or Firm—Juettner Pyle & Lloyd

[57] ABSTRACT

A method to determine the delivery rate and delivery volume per unit of time of a liquid involves connecting one end of a sealed tube to the outlet of the pump, with the other end being provided with a pressure sensor. The pump is activated to pump liquid in to the tube, and air pressure readings are obtained at time intervals. The measured pressures may be used to determine the delivery rate of the pump. The delivery volume (V) is determined by the formula $V = VO \times A/(A+PO)$, wherein VO is the total tube volume, A is the measured air pressure, and PO is the absolute air pressure at the test beginning. Volumes not delivered by the pump due to back pressure may be determined by filling the tube with liquid and measuring the increase in liquid pressure per unit of time against the known delivery rate of the pump.

4 Claims, 1 Drawing Sheet

METHOD AND APPARATUS FOR DETERMINING DELIVERY AMOUNTS AND RATES OF PUMPS IN THE MEDICOTECHNICAL FIELD

BACKGROUND OF THE INVENTION

This invention relates to a testing method for determining delivery rates in delivery systems, such as pumps, in particular injection- or infusion-type pumps, as well as a testing device for said pumps. The present invention is especially concerned with the checking and measurement of the delivery rate, the delivery amount, the maximum shut-off pressure and the bolus amount of pumps, with the bolus amount being defined as the additional delivery volume which is supplied corresponding to pressure drop due to the compressibility of the entire pump system. These parameters should be checked in injection- and infusion-type pumps at regular intervals because health and life of a patient may depend on the correct value of such parameters.

So far, the delivery rate of an injection-type pump has been determined indirectly through a displacement measurement of the advancing syringe-type piston. A mechanical dial gauge is clamped within the syringe receiving cavity of the injection-type pump and the injection-type PUMP is operated by means of a timer for a specific period of time. At the end of this period the distance covered by the syringe-type piston, which has been advanced by a threaded spindle of the pump, is read on the dial gauge. This displacement measurement has the disadvantage that a precise reading of the measured values and strict observance of the selected time interval are difficult to carry out. As a result, the delivery rate of the injection-type pump cannot be determined in a reliable way and with the necessary preciseness.

Moreover, this indirect measurement of the delivery rate is very troublesome and time-consuming.

SUMMARY OF THE INVENTION

It is the object of the present invention to provide a method for measuring the above-mentioned parameters of all common types of delivery systems, such as pumps, in particular, injection- and infusion-type pumps. It is also an object to provide a testing device for such pumps.

In accordance with the present invention, the delivery amount of a pump to be tested is determined by connecting an air-filled measuring conduit, such as a tube, to the pump and to a pressure measuring device, with the volume of the measuring system between pump and pressure measuring device, i.e. predominantly the measuring tube and the associated connections, being known and substantially constant. The pump is activated, and liquid, preferably water, is fed at a constant delivery rate into the measuring tube. The increase in air pressure within the closed measuring tube is measured, and that the delivery amount of the pump is calculated on the basis of the measured pressure values of the non-linear curve of the pressure increase.

The delivery amount of the pump is calculated according to the following formula:

$$V = VO \cdot A / (A + PO) \quad (1)$$

where
A = actual pressure measurement value
P = actual absolute pressure
PO = absolute pressure at test beginning
V = actually filled tube volume
VO = total tube volume The above-mentioned conditional equation is derived as follows:

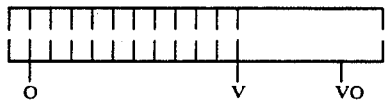

$$P = PO \cdot VO / (VO - V) \quad (2)$$

$$A = P - PO = PO \cdot V / (VO - V) \quad (3)$$

$$A = PO \cdot V / (VO - V) \quad (4)$$

Furthermore, the time is measured in the method of the invention, in order to determine the rate of delivery for the corresponding delivery amount of the pump.

The shut-off pressure of the pump is sensed as a maximum value during pressure measurement.

In a subsequent, second test step according to the invention, the volume of the measuring operation may be repeated with the modification that the measuring system between pump and pressure measuring device is fulled with water without any bubbles. Thereafter, the pump which feeds liquid at a constant delivery rate into the measuring tube, is again activated, and the pressure increase inside the closed measuring system, as well as the time is measured again. This allows compressibility of the pump system to be determined on the basis of a pressure function.

A measurement curve may be derived wherein the delivery amount is plotted over a time interval. The bolus amount of the injection- or infusion-type pump to be tested can be determined for this delivery amount curve, wherein a measured pressure value is assigned to the measured time. Furthermore, a specific delivery amount can then be assigned to the measured times on the basis of the result of the test method according to the present invention, so that, a measurement curve is obtained wherein different pressure values correspond to delivery amounts which are also representative of the respective bolus amounts.

The real pumping capacity of the system at constant pressures may be derived from the measurement curves of the two test steps, as well as the associated bolus amounts caused by a pressure drop in the system. As a result, the actual delivery volume at all possible and variable pressure ratios 13.

With the method of the invention, the relevant pump parameters can be determined quickly and easily, so that these values can be quickly monitored at regular intervals.

The inventive testing device for pumps, in particular injection-or infusion-type pumps, comprises a sensitive pressure transducer, a measuring conduit of a known, substantially constant volume, which is connected to the pressure transducer at one end and to the pump to be tested at the other end. A computing and evaluating device having an internal clock is connected to the pressure transducer. The measuring conduit is preferably a measuring tube which is connected to the testing device, such as by a Luer-Lock tube connection. The total volume of the measuring system between the pump to be tested and the pressure transducer, namely of the measuring tube, including the associated connection lines, is known and is entered into the computing and evaluating device.

The testing device has a pocket calculator-like preferably housing. At least one graphic display and at least two operator buttons are provided and connected to the computing and evaluation device.

Furthermore, the testing device which may be designated as a pump testing computer is equipped with a serial RS 2320 connection through which a report as well as a graphic evaluation of the test can be printed out. It is also within the scope of the present invention to connect an evaluation computer is connected to the testing device of the invention.

Furthermore, that the computing and evaluating device may be equipped with a single-chip microcomputer which is coupled through a special integrating A/D interface to the pressure transducer. This pressure transducer determines the necessary pressure values which are required for the calculation of the delivery rate, the delivery amount, the shut-off pressure and the bolus volume, as has already been described above in more detail.

Moreover, the analog interface unit may work according to a modified charge-balancing principle. This conversion method is not a sampling method, but an integrating measuring method. Such a method it is especially immune to interference and largely independent of component tolerances.

The testing device of the invention may also operate in a dialog-oriented mode. All test algorithms of the equipment are stored as action dialogs, so that the operator of the pump testing computer is guided through the testing procedure. Maloperations are most of the time recognized and corrected by the test computer in dialog mode. The device of the invention is thus very easy to handle.

DESCRIPTION OF THE PREFERRED EMBODIMENTS

Figure 1:
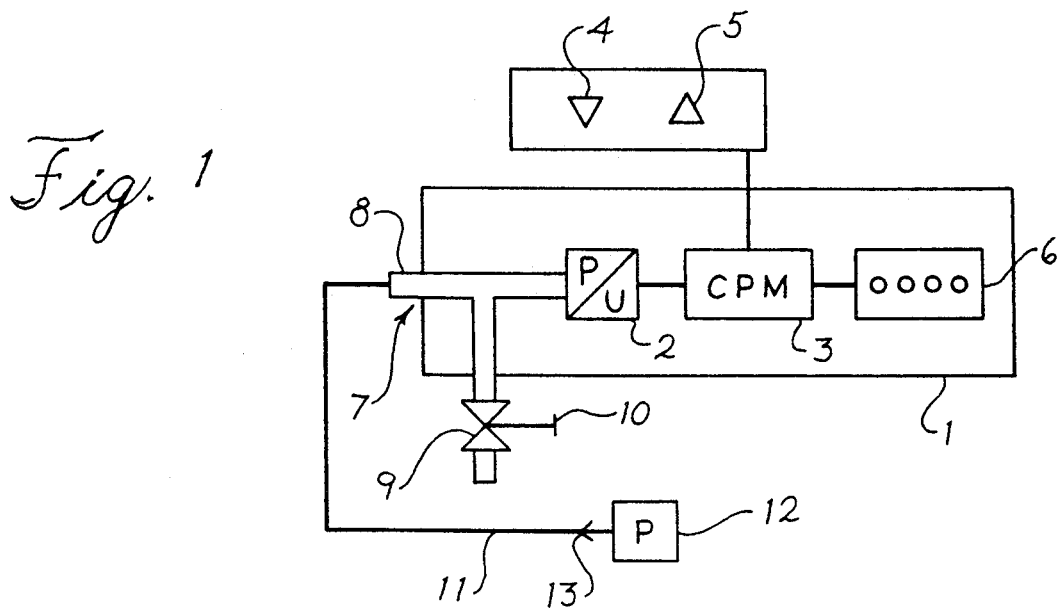
FIG. 1 is a schematic illustration of the apparatus employed to carry out the method of the present invention.

In a pocket calculator-like housing 1, the testing device comprises a pressure transducer 2 which is connected to a computing and evaluation device 3. The computing and evaluation device includes a single-chip microcomputer which is coupled through a special integrating A/D interface to the pressure transducer.

The computing and evaluating device is connected to two operator buttons 4, 5 and a graphic display 6.

The pressure transducer 2 is connected to a branch of a T-shaped conduit, generally indicated at 7, having a inlet branch 8 in the form of a Luer-Lock connection and a third branch connected to a shut-off valve 9. The valve may be operated manually or electronically. One end of a measuring tube 11 is connected to the inlet 8 branch of the T-shaped conduit 7, and the other end is connected at connection point 13 to the pump 12 to be tested.

The volume of the measuring system between pump 12 and pressure transducer 2, i.e. the volume of measuring tube 11, including the pump connection 13, the Luer-Lock connection 8 and the T-shaped connection member 7, is known and substantially constant due to the rigid materials used.

The parameters which correspond to the pump to be tested are selected with the aid of operator buttons 4, 5 prior to a testing operation. The graphic display 6 shows the measurement or pressure curves as they are determined.

Prior to the second measuring step in which the measuring system is filled with water between pump 12 and pressure transducer 2, valve 9 is first opened, so that all air within the measuring system can exit, whereupon, with a bubble-free filling, valve 9 is of course closed before the pump is put into operation for the second measuring operation.

The operation of the device of the present invention will now be described in connection with a pump that is employed to deliver liquids under pressure to a patient, for example, into a vein of a human. Such pumps are well known and are designed to deliver a constant volume per unit of time, but the actual delivered volume may change as the age of the pump increases. Also, the back pressure to the pump will cause the elastic parts thereof to expand and will cause a volume of liquid to be delivered which is less than the expected amount. The volume of the undelivered amount is referred to herein as the "bolus volume or amount." Also, there is a maximum pressure, usually about 2 bar, at which the pump is automatically switched off, in case, for example, of incorrect connection to a patient.

As described herein, the empty tube at atmospheric pressure is connected to the outlet of the pump, and a pressure sensor is at the other sealed end of the tube. The sensor is connected to a computer having a clock to enable a readout of the increasing gas pressure at definite time intervals as liquid is pumped into the tube.

Figure 2:
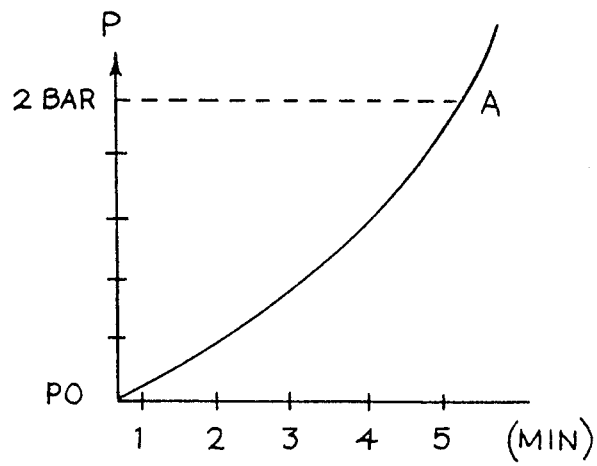
FIG. 2 is a graph which plots gas pressure versus time, from which the delivery rate of a pump may be determined.

A typical graph of pressure readings versus time is shown below in FIG. 2.

The volume delivered may be automatically calculated from equation (1) and would typically appear as a straight line as shown below in FIG. 3.

To determine the bolus amount of the pump, the tube is first filled with water, and the pump is operated. Since the water is substantially incompressible, the pump is only operated for a short period until shutoff pressure is reached.

Figure 3:
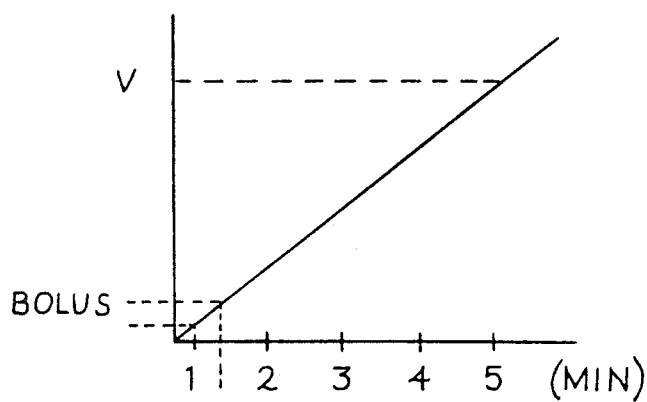
FIG. 3 is a graph which plots liquid pressure versus time, from which undelivered volumes due to back pressure on a pump may be determined.

As shown in FIG. 3, if the pumps has a switch off pressure of 2 bar, and is actually switched off after 1.5 minutes, the bolus amount at this pressure can be determined as shown in FIG. 3. If one wished to determine the bolus amount at 1 bar, for example, and this liquid pressure is reached after one minute of operation, the bolus amount or volume can be plotted on FIG. 3. Hence, this measurement determines the volume of expected delivery which was not delivered due to back pressure on the pump. The device in this instance measures liquid pressure at time intervals, the latter being plotted on the delivery rate graph.

As noted above, the two tests are preformed to precisely determine the delivery rate and volume of a pump, and the pumping time is adjusted accordingly to assure delivery of the correct amount.

I claim:

1. A method for determining the delivery volume and delivery rate of injection and infusion type pumps, said method comprising the steps of:

(a) connecting one end of an air filled tube at atmospheric pressure (PO) to the pump and the other end of the tube to a pressure measurement device, with the air volume (VO) of the tube between the pump and pressure measurement device being sealed and known;

(b) activating the pump and feeding liquid at a constant delivery rate into the tube;

(c) measuring the time at unit intervals;

(d) measuring the air pressure (A) in the tube at said time intervals during activation of the pump;

(e) calculating the delivery volume (V) of the pump on the basis of the measured air pressures according to the formula $$V = VO \times \frac{A}{(A + PO)};$$

(f) determining the delivery rate of the pump as a function of delivery volume per unit time interval.

2. The method of claim 1 wherein the pump has an automatic maximum shut-off liquid pressure, and said liquid pressure is sensed by the air pressure measuring device as a maximum value.

3. The method of claim 1 wherein the pump has a bolus volume due to back pressure on the pump, and wherein, as a separate and new test, the volume of the tube is filled with liquid prior to the activation of the pump, the pump is activated, and the liquid pressure is measured by the pressure measuring device at new time intervals to determine the bolus volume based on the previously determined delivery rate of the pump.

4. The method of claim 3 wherein the delivery rate of the pump at unit time intervals is first plotted, and the liquid pressure increase per unit time interval is used to determine bolus volume at a given pressure.

* * * * *